(12) United States Patent
Ring

(10) Patent No.: US 8,372,041 B2
(45) Date of Patent: Feb. 12, 2013

(54) IN-LINE FLUID TRANSFER DEVICES AND AMBULATORY INFUSION DEVICES INCLUDING THE SAME

(75) Inventor: Lawrence Scott Ring, Valencia, CA (US)

(73) Assignee: The Alfred E. Mann Foundation for Scientific Research, Santa Clarita, CA (US)

( * ) Notice: Subject to any disclaimer, the term of this patent is extended or adjusted under 35 U.S.C. 154(b) by 714 days.

(21) Appl. No.: 12/437,978

(22) Filed: May 8, 2009

(65) Prior Publication Data

US 2010/0286614 A1    Nov. 11, 2010

(51) Int. Cl.
*A61M 1/00* (2006.01)

(52) U.S. Cl. .................................... 604/151

(58) Field of Classification Search .......... 604/149, 604/151–157
See application file for complete search history.

(56) References Cited

U.S. PATENT DOCUMENTS

| | | | |
|---|---|---|---|
| 4,808,089 A * | 2/1989 | Buchholtz et al. ............ 417/417 |
| 4,883,467 A | 11/1989 | Franetzki et al. | |
| 6,746,212 B2 | 6/2004 | Payne | |
| 6,796,777 B2 | 9/2004 | Falk et al. | |
| 6,932,584 B2 | 8/2005 | Gray et al. | |
| 7,066,915 B2 | 6/2006 | Olsen | |
| 7,150,741 B2 | 12/2006 | Erickson et al. | |
| 8,292,601 B2 | 10/2012 | Ring | |
| 8,323,247 B2 | 12/2012 | Ring | |
| 2002/0173773 A1 | 11/2002 | Olsen | |
| 2004/0127852 A1 | 7/2004 | Gray et al. | |
| 2005/0013717 A1 | 1/2005 | Lee | |
| 2006/0210410 A1 | 9/2006 | Mokler | |
| 2008/0139996 A1* | 6/2008 | Bowman et al. ............... 604/67 |
| 2008/0234638 A1 | 9/2008 | Antonio et al. | |
| 2010/0284837 A1 | 11/2010 | Ring | |
| 2010/0286613 A1 | 11/2010 | Ring | |

OTHER PUBLICATIONS

Office Action dated Feb. 17, 2011 in related U.S. Appl. No. 12/437,951.
Notice of Allowance dated Jun. 22, 2012 in related U.S. Appl. No. 12/437,927, with allowed claims attached.
Notice of Allowance dated Oct. 5, 2012 in related U.S. Appl. No. 12/437,951, with allowed claims attached.
Office Action dated Dec. 1, 2011 in related U.S. Appl. No. 12/437,951.
Office Action dated Feb. 28, 2012 in related U.S. Appl. No. 12/437,927.

* cited by examiner

*Primary Examiner* — Nicholas Lucchesi
*Assistant Examiner* — Melissa A Snyder
(74) *Attorney, Agent, or Firm* — Henricks, Slavin & Holmes LLP

(57) ABSTRACT

Fluid transfer devices for use in, for example, ambulatory infusion devices and infusions devices including fluid transfer devices.

37 Claims, 9 Drawing Sheets

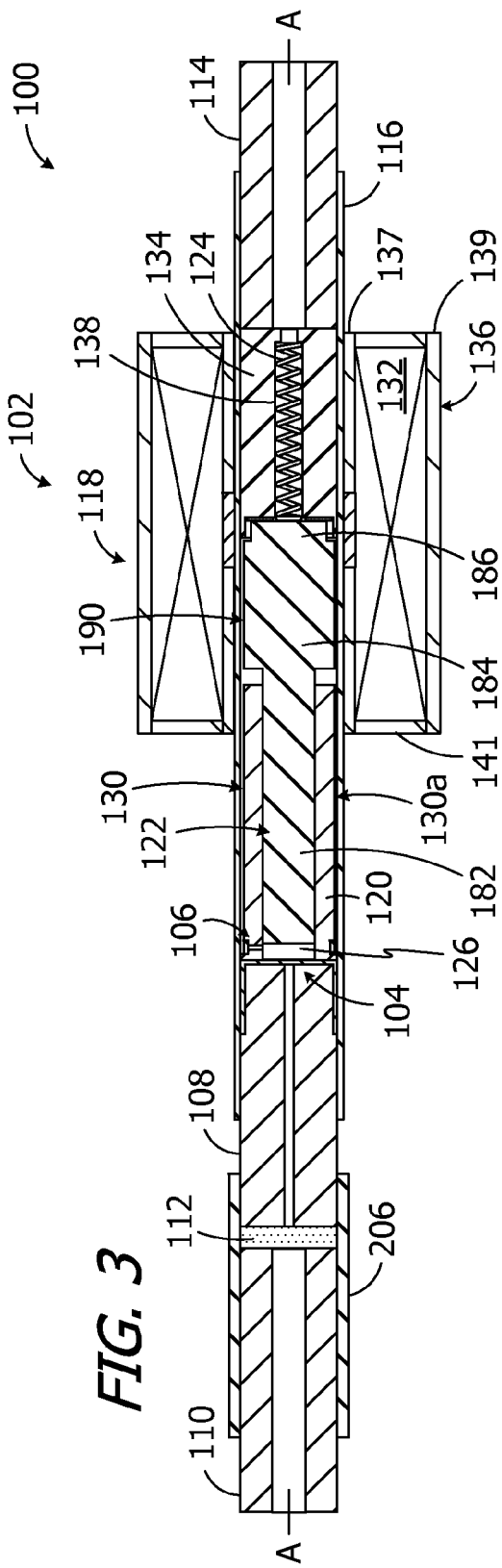
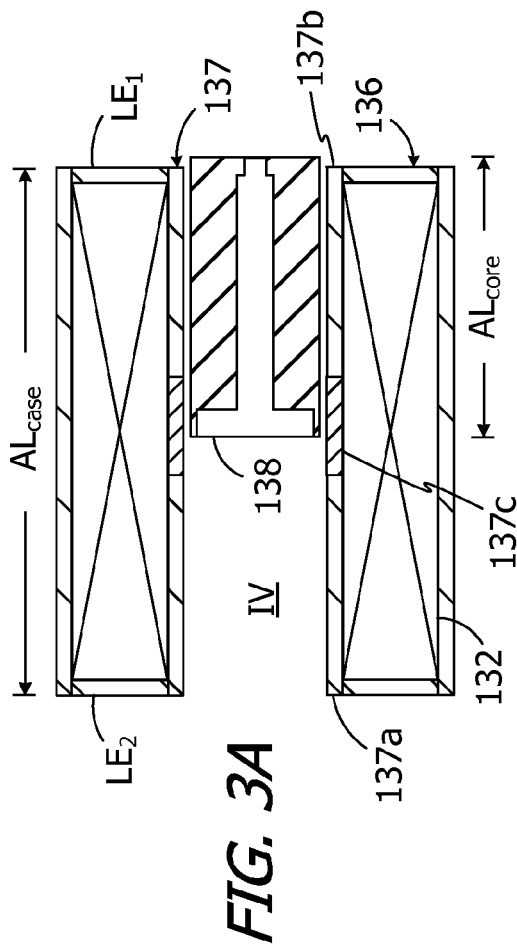

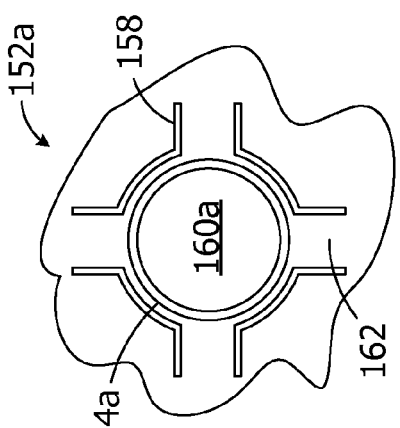
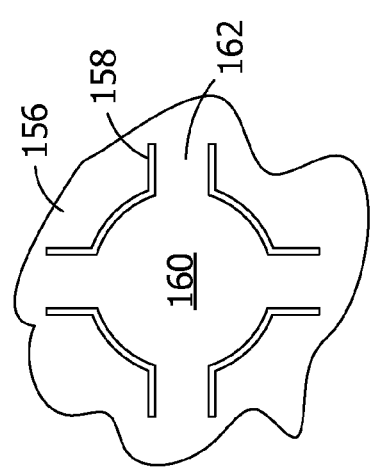
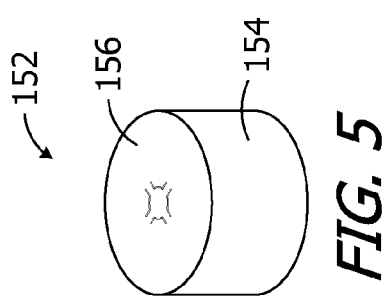
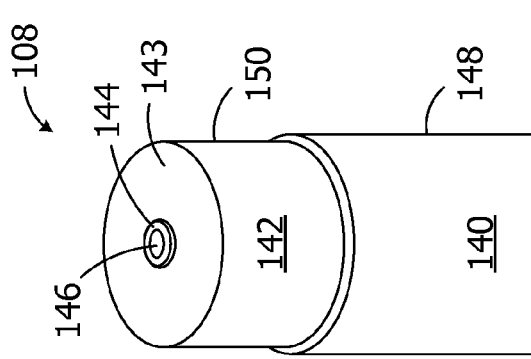
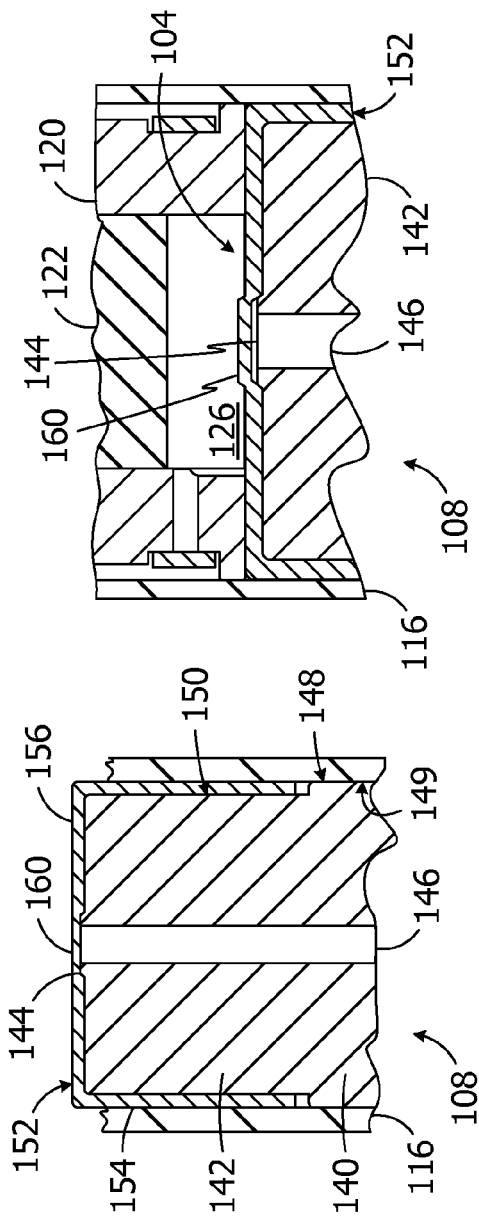
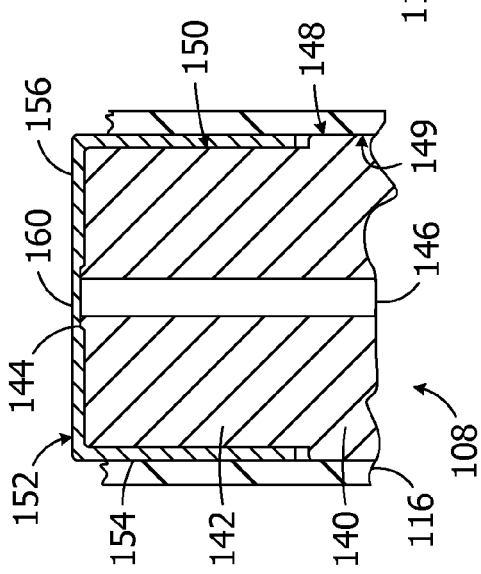

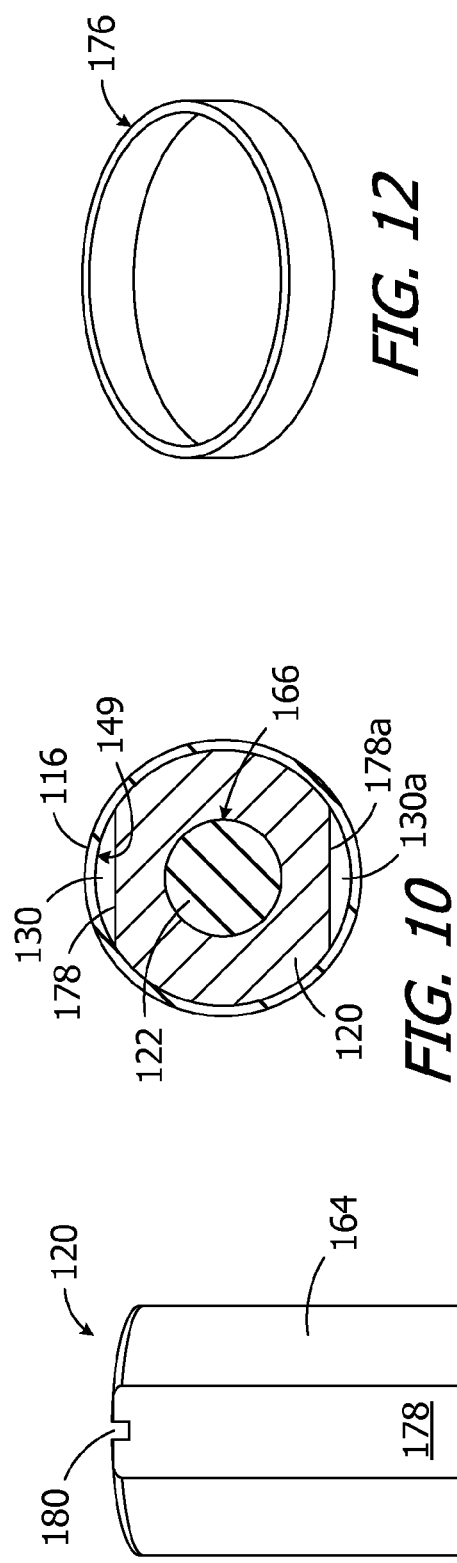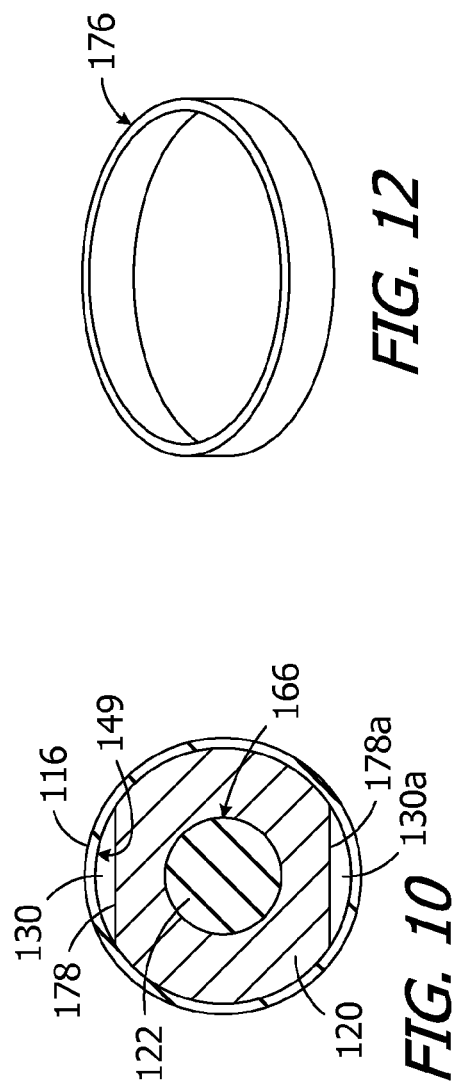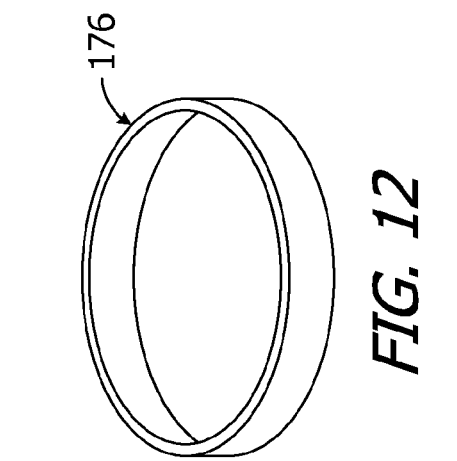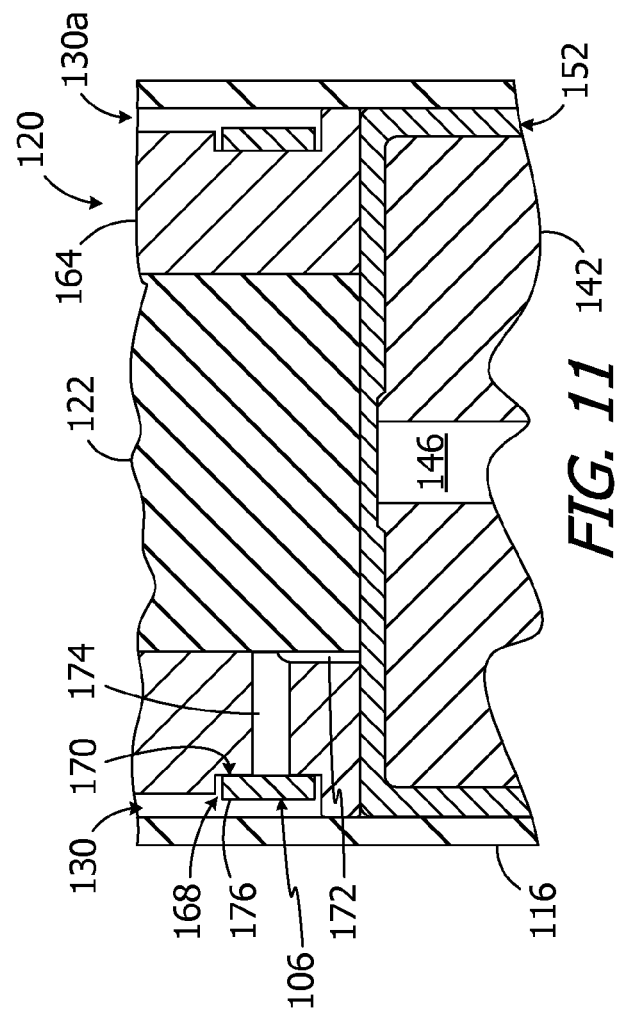

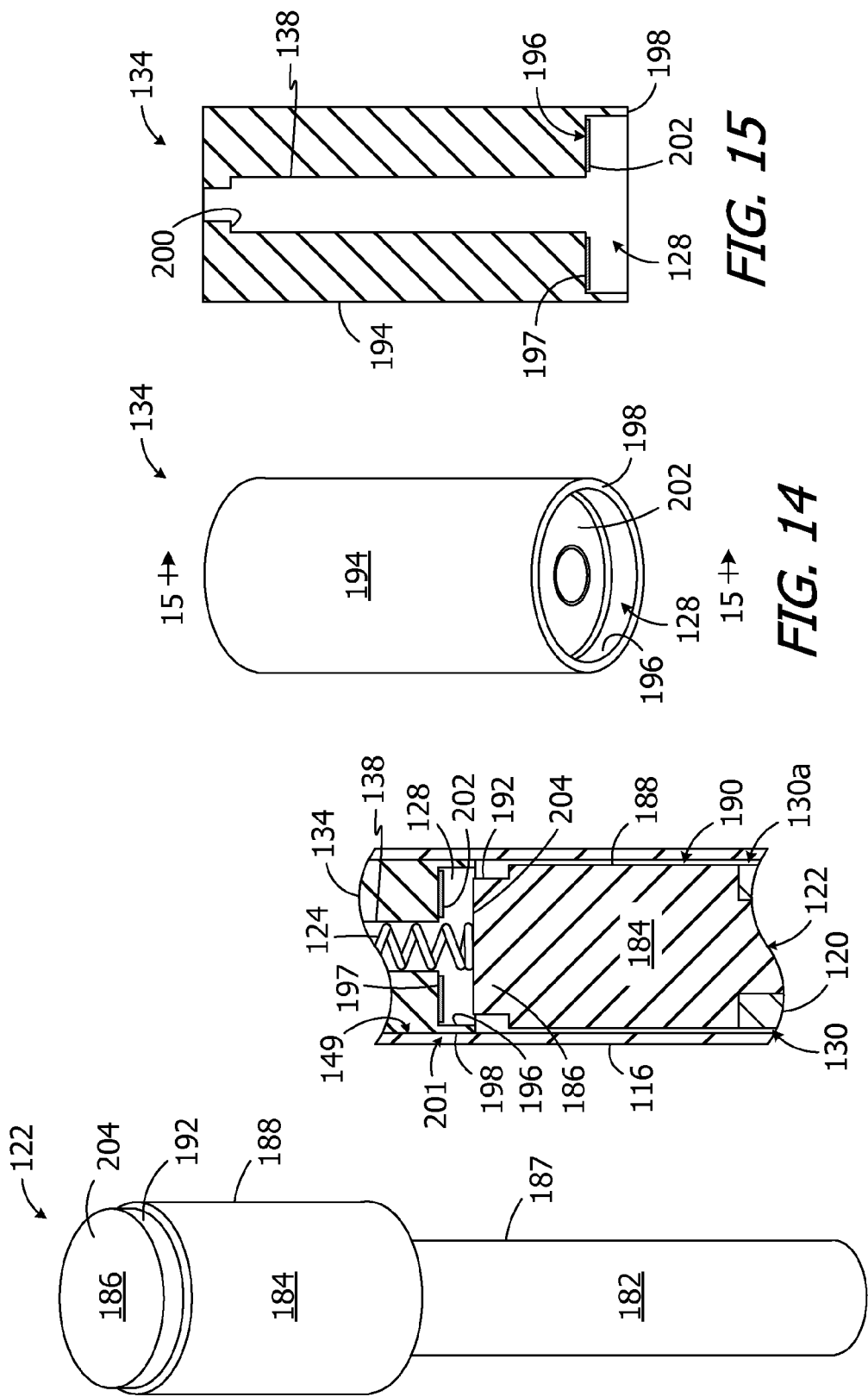

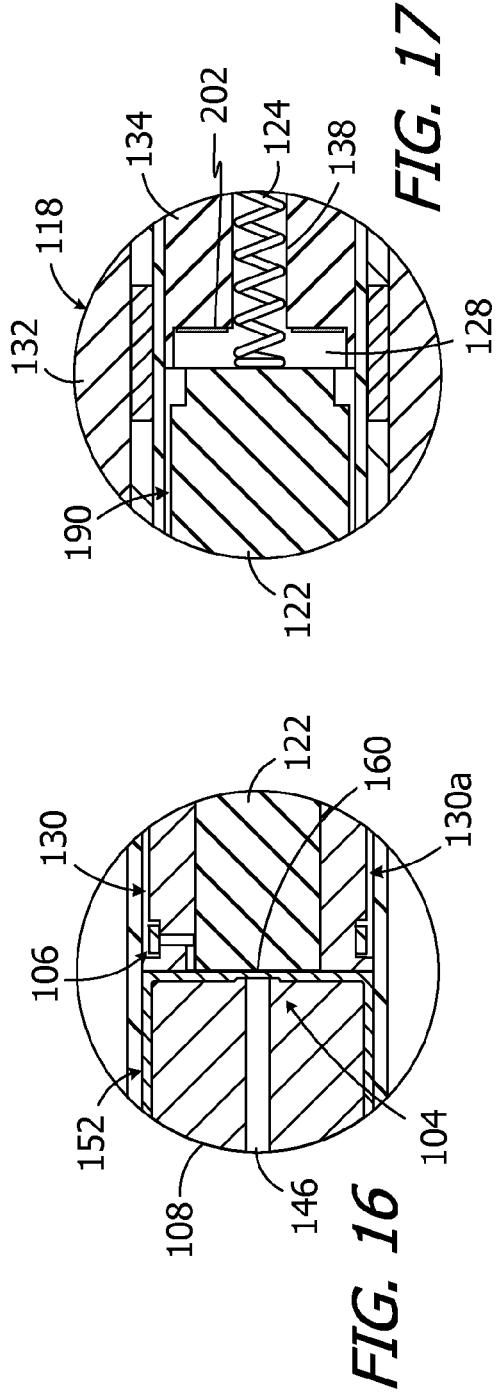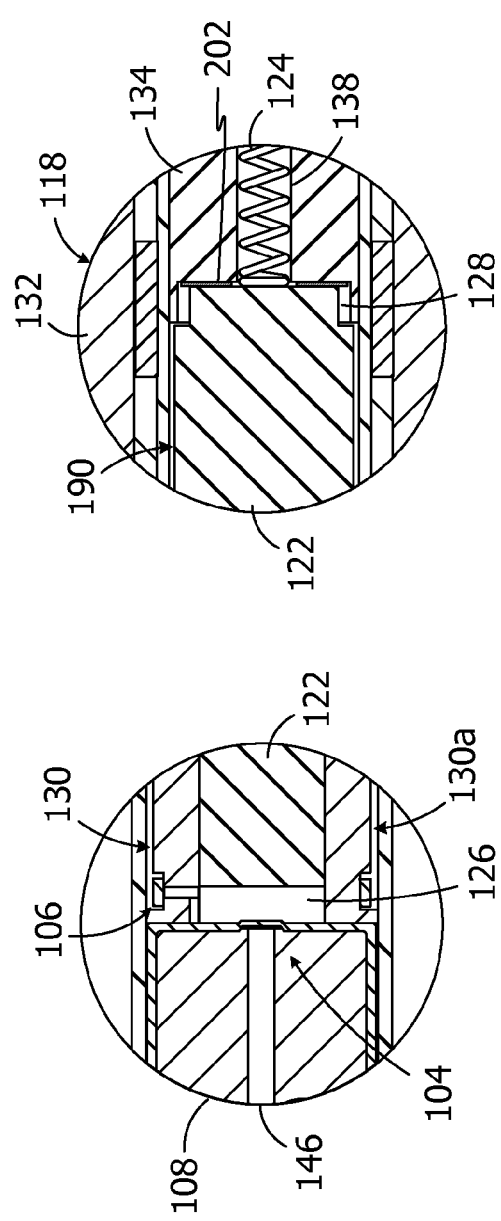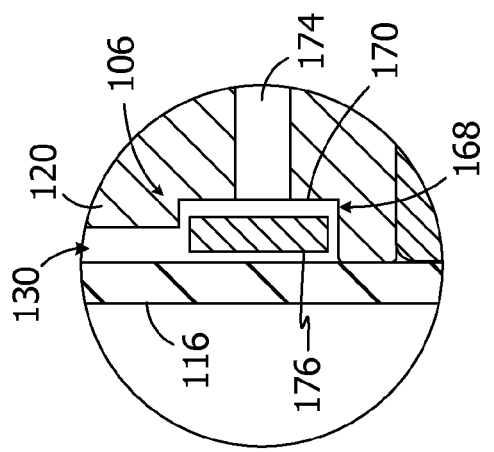

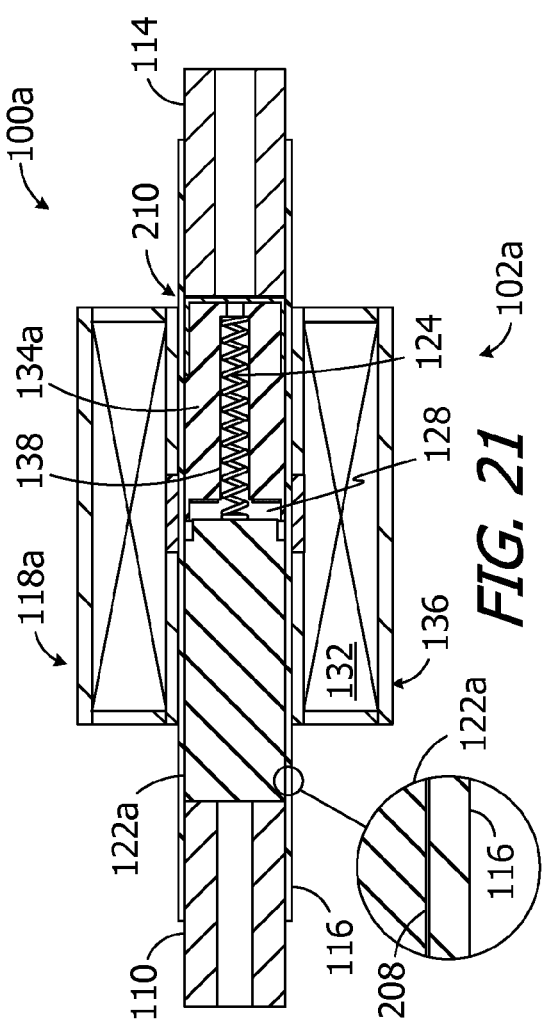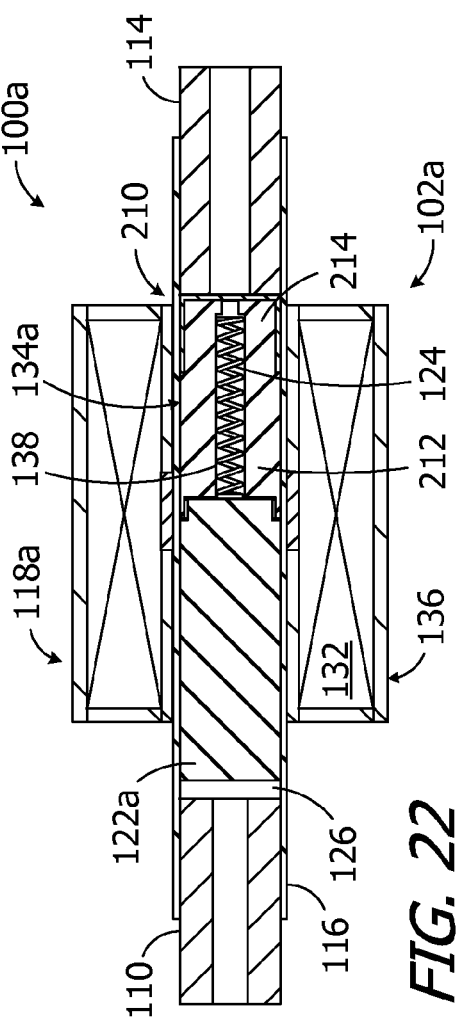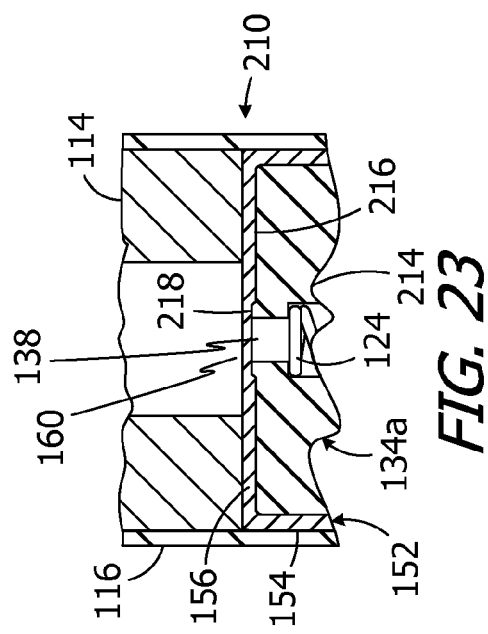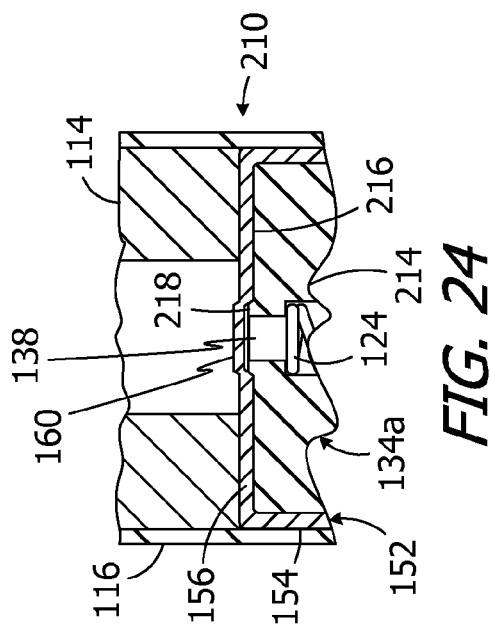

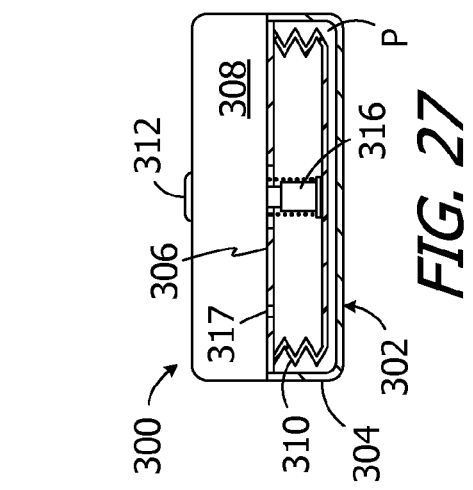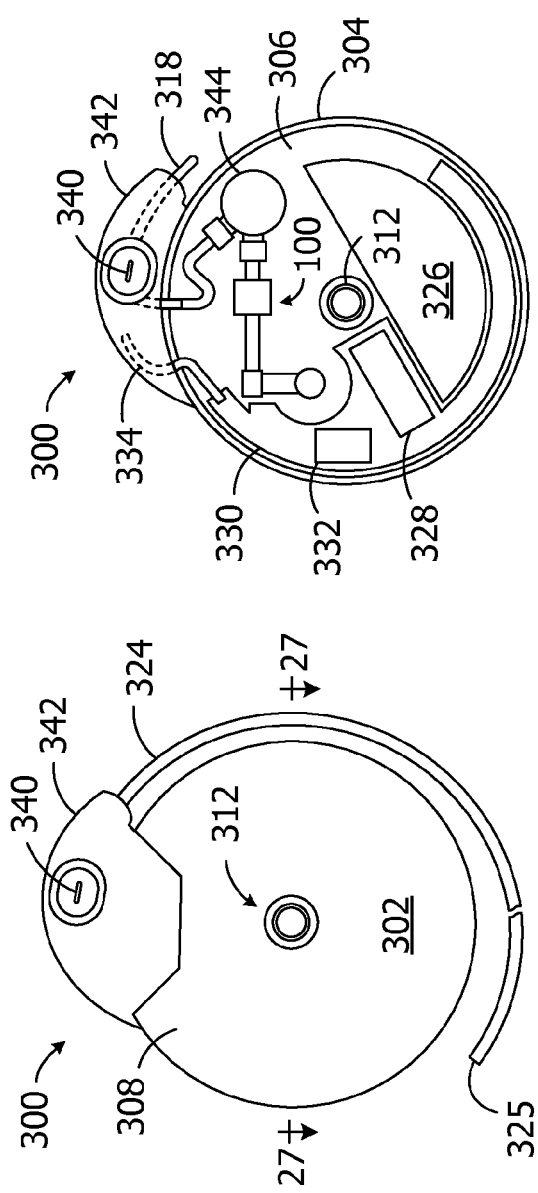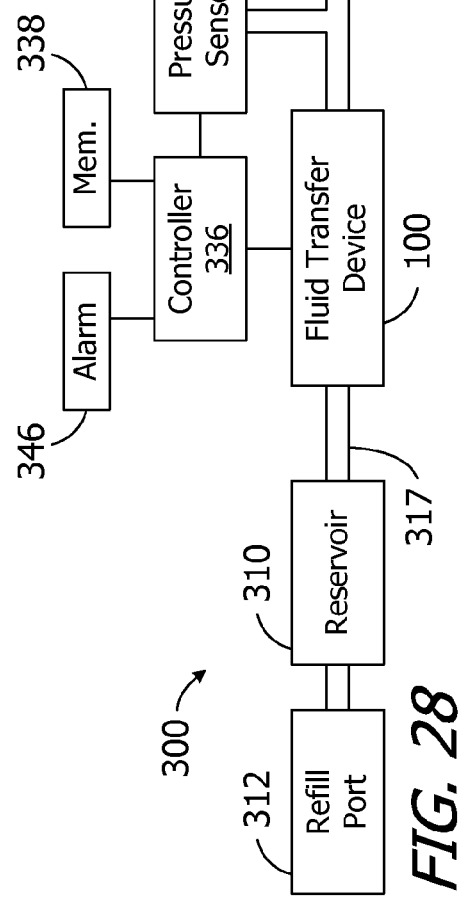

IN-LINE FLUID TRANSFER DEVICES AND AMBULATORY INFUSION DEVICES INCLUDING THE SAME

BACKGROUND

1. Field

The present devices relate generally to pumps, fluid transfer devices, and apparatus including the same.

2. Description of the Related Art

A wide variety of fluid transfer devices, which commonly include a pump and one or more valves, are configured to transfer relatively small volumes of fluid per actuation of the pump. Implantable (or otherwise ambulatory) infusion devices, for example, frequently include a fluid transfer device that has an electromagnet pump and one or more valves. Examples of conventional electromagnet pumps for ambulatory infusion devices are disclosed in U.S. Pat. No. 6,796,777 to Falk et al. and U.S. Pat. No. 6,932,584 to Gray. Pipettors are another exemplary area where pumps and fluid transfer devices that transfer relatively small volumes of fluid per pump actuation are employed.

The present inventor has determined that conventional fluid transfer devices and pumps for small volume applications are susceptible to improvement. For example, the present inventor has determined that conventional electromagnet pumps and fluid transfer devices are relatively complex in that they include a plethora of very small components, many of which are difficult to produce and assemble, and that the complexity may reduce reliability. The present inventor has also determined that the amount of power consumed by conventional electromagnet pumps could be reduced. The present inventor has also determined that the amount of ullage in conventional pumps, which makes it difficult to pump gas bubbles, can be reduced.

Fluid transfer devices in accordance with at least some of the present inventions include a pump and a valve. The valve, which may be an inlet valve or a one-way outlet valve, includes a valve base, with a seal surface, and a resilient structure mounted in tension on the valve base. The resilient structure has a valve member movable between a closed state where the valve member engages the seal surface and an open state where at least a portion of the valve member is spaced apart from the seal surface.

Fluid transfer devices in accordance with at least some of the present inventions include a valve and a pump. The valve, which may be an inlet valve or a one-way outlet valve, includes a seal surface and a resilient membrane with a least one narrow opening and a valve member associated with the narrow opening. The resilient membrane is movable between a closed state where the valve member engages the seal surface and an open state where at least a portion of the valve member is spaced apart from the seal surface. The pump includes a piston that is biased to a rest position and is movable to a pull-back position. In those instances where the valve is an inlet valve, the piston holds the valve member against the seal surface when in the rest position.

Fluid transfer devices in accordance with at least some of the present inventions include an external housing member, an internal housing member defining a piston lumen, an outer surface having a perimeter, and a bypass aperture, a bypass channel in fluid communication with the bypass aperture, a resilient valve member that extends around the internal housing member and over the bypass aperture outlet, and a piston carried within the piston lumen.

Fluid transfer devices in accordance with at least some of the present inventions include an external housing tube, an internal housing tube defining a piston lumen and a bypass aperture, a bypass channel defined by the external housing tube and the internal housing tube in fluid communication with the bypass aperture, a valve member associated with the bypass aperture, and a piston carried within the piston lumen.

Fluid transfer devices in accordance with at least some of the present inventions include an electromagnet and a piston. The electromagnet has a coil, a case, and a core having a fluid lumen, and at least a portion of the core is located within the internal volume defined by the case. The piston, which has at least a portion that is magnetic and is located within the internal volume defined by the case, is movable relative to the core between a rest position and a pull-back position adjacent to the core, and is biased to the rest position.

Fluid transfer devices in accordance with at least some of the present inventions include an inner pump tube defining a piston lumen, an outer pump tube, a piston that does not include a fluid lumen and has at least a portion thereof mounted within the piston lumen such that a capillary seal is formed between the piston and the inner pump tube, an electromagnet including a coil carried outside the outer pump tube and a core having a fluid lumen carried inside the outer pump tube, a bypass channel defined at least in part by in the inner and outer pump tubes, and a bypass valve.

Fluid transfer devices in accordance with at least some of the present inventions include a housing defining a piston lumen, a piston stop including a fluid lumen, a piston which does not include a fluid lumen. The first end of the piston and the piston lumen together define an inlet chamber, and the second end of the piston and the piston stop together define an outlet chamber. The piston is movable between a first position where the volume of the inlet chamber is minimized and a second position where the piston abuts the piston stop and the prevents flow into the inlet of the piston stop lumen.

Infusion devices in accordance with at least some of the present inventions include a reservoir, an infusion device outlet, and a fluid transfer device as described in the preceding paragraphs of this Summary operably connected to the reservoir and the infusion device outlet.

BRIEF DESCRIPTION OF THE DRAWINGS

Detailed descriptions of exemplary embodiments will be made with reference to the accompanying drawings.

FIG. 3 is a section view showing the fluid transfer device illustrated in FIG. 1 in an actuated state.

FIG. 3A is a section view showing a portion of the fluid transfer device illustrated in FIG. 1.

FIG. 4 is a perspective view of an inlet tube including a valve structure in accordance with one embodiment of a present invention.

FIG. 5 is a perspective view of a valve structure in accordance with one embodiment of a present invention.

FIG. 6 is a plan view of a portion of the valve structure illustrated in FIG. 5.

FIG. 6A is a plan view of a portion of a valve structure in accordance with one embodiment of a present invention.

FIG. 7 is a section view of the inlet tube and valve structures illustrated in FIGS. 4-6 showing the valve in a closed state.

FIG. 8 is a section view of the inlet tube and valve structures illustrated in FIGS. 4-6 showing the valve in an open state.

FIG. 9 is a front view of a pump tube in accordance with one embodiment of a present invention.

FIG. 10 is a section view taken along line 10-10 in FIG. 1.

FIG. 11 is an enlarged view of a portion of FIG. 2.

FIG. 12 is a perspective view of a valve structure in accordance with one embodiment of a present invention.

FIG. 13 is a perspective view of a piston in accordance with one embodiment of a present invention.

FIG. 13A is an enlarged view of a portion of the fluid transfer device illustrated in FIG. 2.

FIG. 14 is a perspective view of an electromagnet core in accordance with one embodiment of a present invention.

FIG. 15 is a section view take along line 15-15 in FIG. 14.

FIG. 16 is an enlarged view of a portion of FIG. 2.

FIG. 17 is an enlarged view of a portion of FIG. 2.

FIG. 18 is an enlarged view of a portion of FIG. 3.

FIG. 19 is an enlarged view of a portion of FIG. 3.

FIG. 20 is an enlarged view showing a valve in an open state.

FIG. 21 is a section view of a fluid transfer device in accordance with one embodiment of a present invention in a rest state.

FIG. 22 is a section view showing the fluid transfer device illustrated in FIG. 21 in an actuated state.

FIG. 23 is a section view of a valve structure in a closed state.

FIG. 24 is a section view of a valve structure in an open state.

FIG. 25 is a plan view of an implantable infusion device in accordance with one embodiment of a present invention.

FIG. 26 is a plan view of the exemplary implantable infusion device illustrated in FIG. 25 with the cover removed.

FIG. 27 is a partial section view taken along line 27-27 in FIG. 25.

FIG. 28 is a block diagram of the exemplary implantable infusion device illustrated in FIGS. 25-27.

DETAILED DESCRIPTION OF EXEMPLARY EMBODIMENTS

The following is a detailed description of the best presently known modes of carrying out the inventions. This description is not to be taken in a limiting sense, but is made merely for the purpose of illustrating the general principles of the inventions. The present inventions are also not limited to use in conjunction with the exemplary implantable infusion devices described herein and, instead, are applicable to other implantable or otherwise ambulatory infusion devices that currently exist or are yet to be developed, as well as other apparatus that employ pumps and fluid transfer devices in relatively low volume per actuation applications. Examples of such apparatus include, but are not limited to, portable (e.g. battery operated) inflation devices such as pressure cuffs, hydraulic cutters, and balloon fillers; microfluidic cooling systems for electronics, such as those which cool individual microprocessor chips; high efficiency micro refrigeration systems; microfluidic pumps for fuel cells, such as small fuel cells for portable computers, cell phones, and the other electronic devices; and microdispensing pumps for pipettors and printers, such as dispensers in stereo lithography machines.

Figure 1:
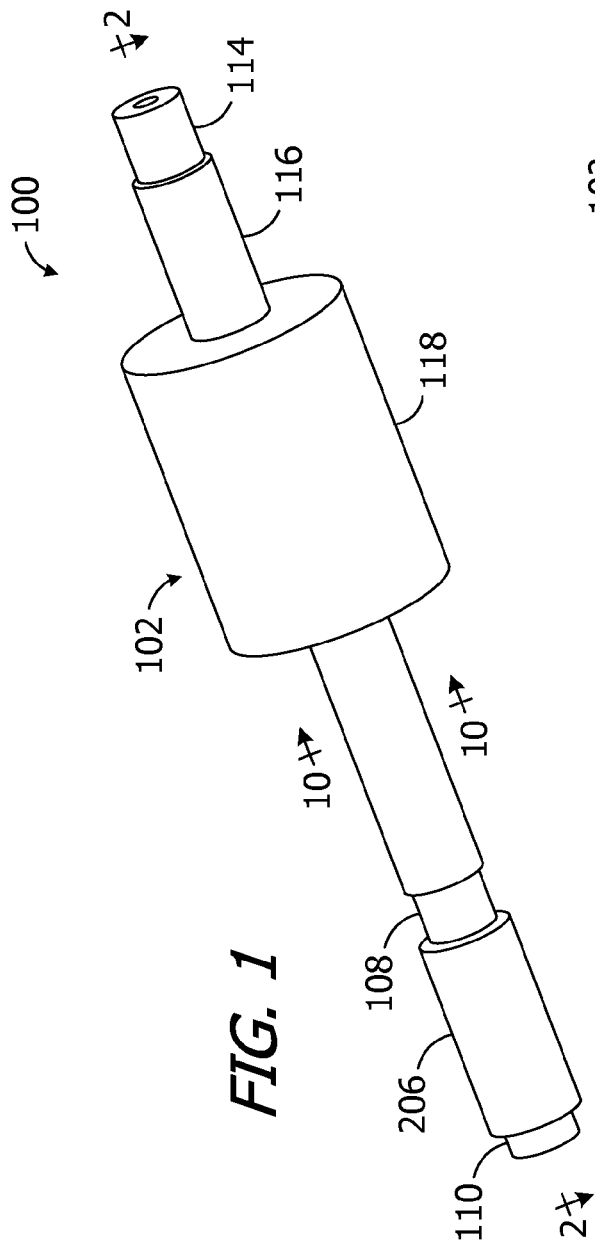
FIG. 1 is a perspective view of a fluid transfer device in accordance with one embodiment of a present invention.
Figure 2:
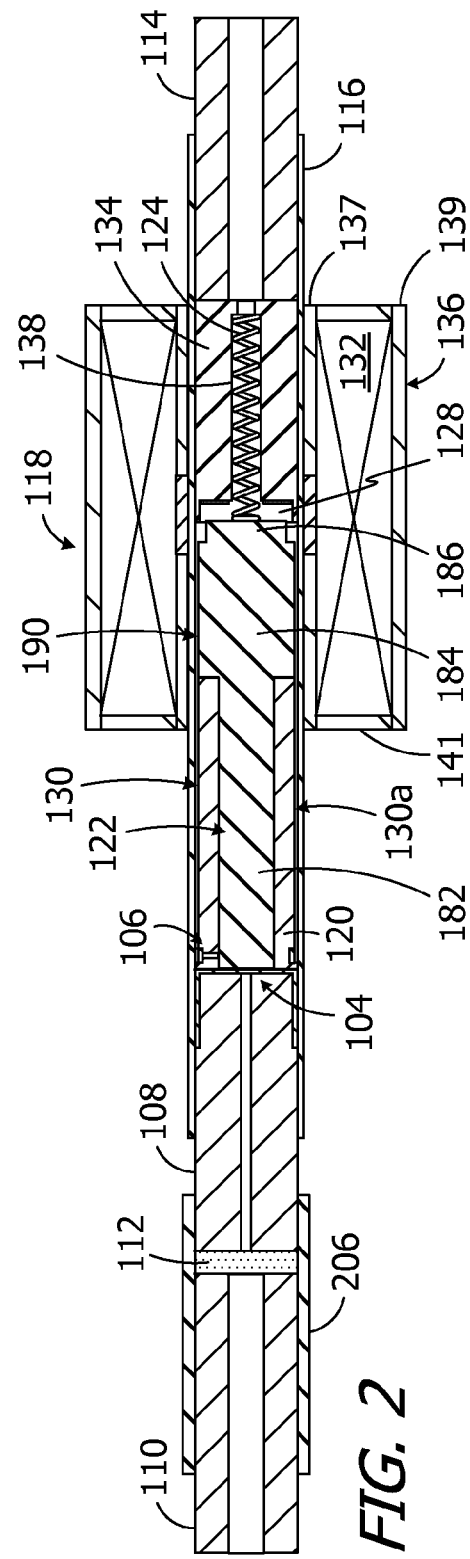
FIG. 2 is a section view taken along line 2-2 in FIG. 1 showing the fluid transfer device illustrated in FIG. 1 in a rest state.
Figure 15A:
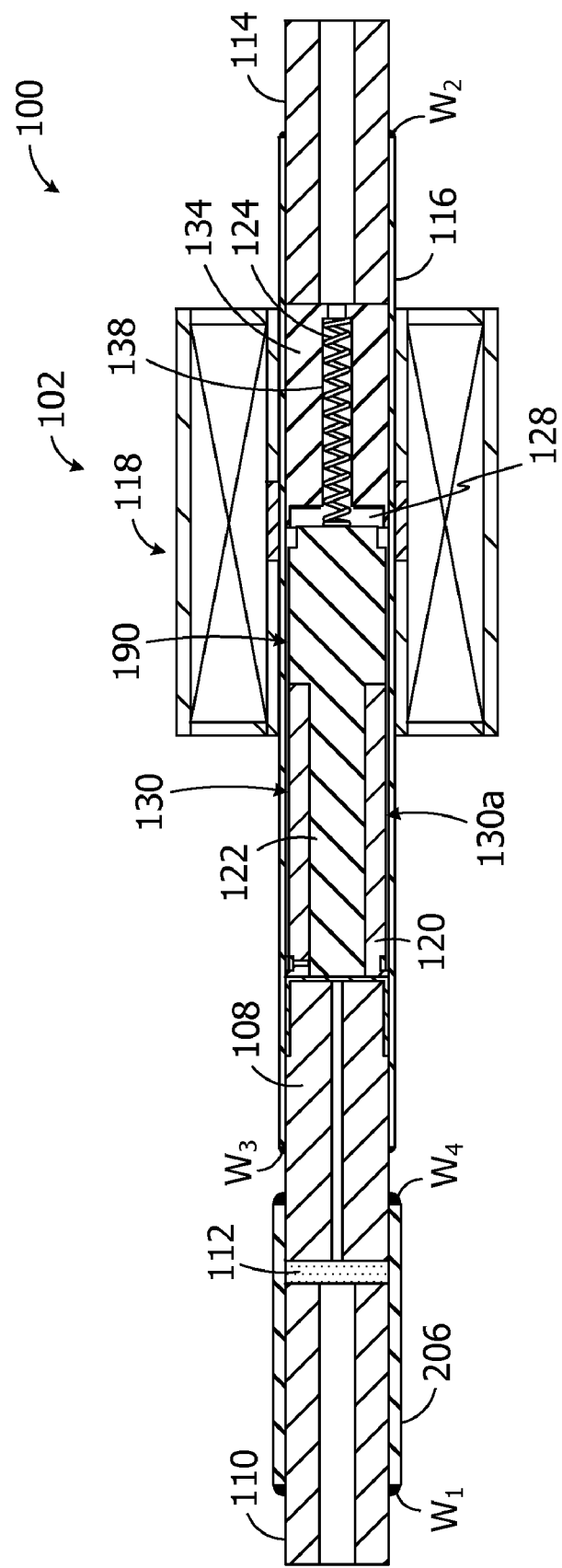
FIG. 15A is a section view showing the fluid transfer device illustrated in FIG. 1 in a rest state.

One example of a fluid transfer device in accordance with at least one of the present inventions is generally represented by reference numeral 100 in FIGS. 1-3. The exemplary fluid transfer device 100 includes a pump 102, an inlet valve 104 (sometimes referred to in the art as a "main check valve") and a bypass valve 106. Inlet tubes 108 and 110 and a filter 112 are associated with one end of the pump 102, and an outlet tube 114 is associated with the other end of the pump. Each of these components is discussed in greater detail below. Also, the welds that are discussed below with reference to FIG. 15A are not shown in FIGS. 1-3 because they may be replaced by other instrumentalities that perform the same function.

The exemplary pump 102 illustrated in FIGS. 1-3 has an outer pump tube 116, an electromagnet 118 that has a portion carried within the outer pump tube and a portion carried on the exterior of the outer pump tube, an inner pump tube 120 that is carried within the outer pump tube, and a magnetic piston 122. In addition to facilitating the assembly of the fluid transfer device 100, the outer pump tube 116 also combines with the inner pump tube 120 and magnetic piston 122 to defines some of the flow channels within the fluid transfer device. Suitable materials for the outer pump tube include, but are not limited to, non-magnetic materials such as titanium, 300 series stainless steels, polysulfone, Kapton, and PEEK. The magnetic piston 122 is biased to the rest position illustrated in FIG. 2 by a spring 124 or other suitable biasing element. An inlet chamber 126 (FIG. 3), which is sometimes referred to in the art as a "pump chamber," is defined between the inlet valve 104 and one end of the magnetic piston 122, and an outlet chamber 128 (FIG. 2) is defined between the other end of the magnetic piston 122 and the electromagnet core 134 (discussed below). The magnetic piston 122 overcomes the biasing force associated with the spring 124, and moves from the rest position illustrated in FIG. 2 to the pull-back position illustrated in FIG. 3, when the electromagnet 118 is energized. The spring 124 drives the magnetic piston 122 back to the rest position when the electromagnet 118 is de-energized. As is discussed in greater detail below with reference to FIGS. 16-20, movement of the magnetic piston 122 to the pull-back position results in a decrease in pressure in the inlet chamber 126. The reduction in pressure within the inlet chamber 126 causes the inlet valve 104 to open and fluid to flow into the inlet chamber. The inlet valve 104 will close once the pressure within inlet chamber 126 is equal to pressure at the inlet tube 108. Movement of the magnetic piston 122 to the pull-back position also drives fluid out of the outlet chamber 128. When the magnetic piston 122 moves back to the rest position, the pressure within the inlet chamber 126 will increase and open the bypass valve 106 so that fluid will flow into the flow channels 130 and 130a (sometimes referred to a "bypass channels") that are located between the inner and outer pump tubes 116 and 120 and extend to the outlet chamber 128. The flow channels 130 and 130a are discussed in greater detail below with reference to FIGS. 9-11.

The exemplary electromagnet 118 illustrated in FIGS. 1-3 includes a coil 132 and a core 134. The coil 132 is carried within a case 136 that is mounted on the exterior of the outer pump tube 116, while the core 134 is carried within the outer pump tube. In addition to forming part of the electromagnet 118, the core 134 includes a lumen 138 that centers the spring 124 and forms part of the fluid flow path and also acts as a piston stop. The core 134 and case 136 may be formed from a magnetic material, such as AL29-4 superferritic stainless steel alloy for the core 134, which contacts fluid, and Hiperco 50 for the case 136, which does not contact fluid. The coil 132, which consists of a wound wire or other conductor, is a hollow structure that extends around the core 134.

The exemplary electromagnet core 134 is discussed in greater detail below with reference to FIGS. 13-15. It should be noted here with reference to FIGS. 3 and 3A, however, that the electromagnet core 134 has an axial length $AL_{core}$ that is substantially less than the axial length $AL_{case}$ of the electromagnet case 136, and that one of the longitudinal ends of the core 134 is adjacent to one of the longitudinal ends of case 136. An "axial length" is a length measured along the longitudinal axis A of the fluid transfer device 100. Depending on the particular embodiment, the core 134 extends from one longitudinal end $LE_1$ of the case 136 to a point located about 30% to 70% of the way to the other longitudinal end $LE_2$ of the case (about 50% in the illustrated embodiment). Put another way, the case 136 defines an internal volume IV that has an axial length which is equal to the axial length $AL_{case}$ of the case. The core 134 is located within a portion of the longitudinal extent of the internal volume. Also, one end of the core 134 extends beyond the longitudinal end $LE_1$ of the case 136 in the illustrated embodiment. The magnetic piston 122, or at least a portion thereof, occupies the remainder of the length of the internal volume of the case 136. Such an arrangement is more efficient that the conventional armature design, where the armature pole is located in spaced relation to the electromagnet, which facilitates longer battery life and/or additional power consuming functionality.

The exemplary electromagnet case 136 illustrated in FIGS. 1-3A includes an inner tube 137, an outer tube 139 and end caps 141. The inner tube 137 has magnetic portions 137a and 137b and a non-magnetic spacer 137c between the magnetic portions (FIG. 3A). Alternatively, the electromagnet case may be fabricated in two cylindrical halves by machining or by metal injection molding. The electromagnet case 136 also includes holes (not shown) to permit the wire leads of the coil 132 to be connected to an energy source.

Turning to FIGS. 4-8, the exemplary inlet tube 108 is a generally cylindrical structure that includes a main portion 140, an inlet valve base 142 with a seal surface 143 that has a protrusion 144, and an inner lumen 146 with an outlet end at the inlet chamber 126. The protrusion 144 reduces the contact area between the seal surface and the movable valve member 160 (discussed below) and, therefore, results in greater sealing pressure than that which would be associated with two flat surfaces. The diameter of the main portion outer surface 148 is essentially equal to the diameter of the inner surface 149 of the outer pump tube 116 and is greater than the diameter of the inlet valve base outer surface 150. In addition to the inlet valve base 142, the inlet valve 104 includes a resilient cup-shaped structure 152 with a cylindrical wall 154 and an end wall 156. The end wall 156 has a plurality of slots 158 that form a movable valve member 160 and a plurality of valve member supports 162 that connect the movable valve member to the remainder of the end wall 156. In its unstressed state (FIG. 5), the inner diameter of the cylindrical wall 154 of the resilient cup-shaped structure 152 is less than the diameter of the inlet valve base outer surface 150. In some implementations, the unstressed (or "relaxed") inner diameter of the cylindrical wall 154 will be about 50% to 95% of the diameter of the inlet valve base outer surface 150. As a result, the resilient cup-shaped structure 152 must be stretched when it is positioned over the inlet valve base 142 which, in turn, pretensions the cup-shaped structure. The pretension pulls the end wall 156, including the movable valve member 160, against the seal surface 143 and seal surface protrusion 144. The resilient cup-shaped structure 152 is held in place by the inlet tube 108 and the inner pump tube 120 after assembly. Adhesive may also be used to secure the resilient cup-shaped structure 152 to the inlet valve base 142 if desired. A seal is formed by the seal surface 143, the end wall 156, the inner pump tube 120, the inlet tube 108, the outer pump tube 116, and the weld $W_3$ (FIG. 15A) or other joining of the outer pump tube 116 and the inlet tube 108.

The inner pump tube 120 and magnetic piston 122, which is biased to the position illustrated in FIG. 2 by spring 124, hold the end wall 156 of the resilient cup-shaped structure 152 against the valve base seal surface 143 in the manner illustrated in FIGS. 7 and 11. The magnetic piston 122 also flattens (or "compresses") the movable valve member 160 against the seal surface protrusion 144. As noted above, movement of the magnetic piston 122 to the pull-back position results in a decrease in pressure within the inlet chamber 126. The reduction in pressure within the inlet chamber 126 allows the pressure at the inlet tube 108 to overcome the pretension force on the movable valve member 160. The valve member 160 will then move away from the seal surface protrusion 144, thereby opening the inlet valve 104 and allowing fluid to flow into the inlet chamber 126 (FIG. 8). More specifically, when some or all of the valve member 160 moves away from the seal surface protrusion 144, fluid will be able to flow through some or all of the slots 158. The pretension force on the valve member 160 will close the inlet valve 104 when the pressure within inlet chamber 126 is equal to pressure within the inlet tube lumen 146.

With respect to materials, the inlet tube 108, as well as inlet tube 110 and outlet tube 114, may be formed from titanium capillary tubing or other suitable tubing. Suitable materials for the resilient cup-shaped structure 152 include, but are not limited to, elastomers with good sealing properties, such as silicone rubber, fluoroelastomers, urethanes, and latex rubber. The material that forms the cylindrical wall 154 and end wall 156 may, in some implementations, be a membrane that is about 0.002 inch to about 0.010 inch thick. Wear protection may be achieved by way of metallization, ceramic ion implantation, foil lamination, plastic film lamination, coatings such as plasma deposited silicate, vacuum deposited parylene, or solution deposited LSR Top Coat from GE Silicones. Turning to manufacturing, the resilient cup-shaped structure 152 may be molded or dip formed. The slots 158 may be formed by die cutting, laser cutting, or molding. In those instances where laser cutting is employed, the inclusion of a small percentage of optically absorptive filler material in the elastomer will ease fabrication.

It should be noted that the present fluid transfer devices are not limited to the illustrated inlet valve 104. The inlet valve 104 is susceptible to a many variations. By way of example, but not limitation, the slots 158 and valve member 160 may have other configurations that also provide minimal opening pressure and fast auto-closure after pressure equalization. For example a spiral slot may be employed. Slots, slits or other narrow openings (i.e. about 0.000 inch to about 0.005 inch) may also be configured such that the valve member consists of a single flap or is divided into quadrants. A coating, such as plasma deposited silicate, vacuum deposited parylene, or solution deposited LSR Top Coat from GE Silicones, may be applied to the slit surfaces to reduce adhesion. In other implementations, a protrusion may be provided on valve member instead of the sealing surface 143. For example, the resilient cup-shaped structure 152a illustrated in FIG. 6A is identical to the cup-shaped structure 152 but for the protrusion 144a on the valve member 160a. In other implementations, a protrusion may be omitted. Other types of inlet valves may be employed in other fluid transfer devices in accordance with at least some of the present inventions. Such alternative inlet valves include, but are not limited to, each of the inlet valves discloses in U.S. Patent Pub. No. 2008/0234638, which is incorporated herein by reference.

Turning to FIGS. 9-12, the exemplary inner pump tube 120 includes a generally cylindrical main body 164 with an internal lumen 166 for the magnetic piston 122. The inner pump tube 120 is also part of the bypass valve 106 and the flow channel 130. With respect to the bypass valve 106, the inner pump tube 120 includes an annular indentation 168 that defines a seal surface 170, a bypass channel 172, and a bypass aperture 174. A resilient annular valve member 176 is positioned within the annular indentation 168 over the bypass aperture 174. When the magnet piston moves from the pull-back position (FIG. 3) to the rest position (FIG. 11), fluid within the inlet chamber 126 (FIG. 3) will be driven through the bypass channel 172 and bypass aperture 174 and will stretch the resilient annular valve member 176 away from the seal surface 170, thereby opening the bypass valve 106 so that fluid will enter the flow channel 130, as is discussed in greater detail below with reference to FIG. 20. The unstressed inner diameter of the resilient annular valve member 176 in the illustrated embodiment is only slightly less than the diameter of the seal surface 170, in order to insure that the opening pressure of the bypass valve 106 is minimized.

Although the shapes of the annular indentation 168 and annular valve member 176 in the illustrated embodiment are such that the interface between the seal surface 170 and annular valve member is flat when viewed in cross-section (FIG. 11), the shape of the annular indentation and/or annular valve member may be adjusted as desired. By way of example, but not limitation, the interface between the seal surface 170 and annular valve member 176 may be curved. This may be accomplished by, for example, configuring the annular indentation 168 such that the seal surface 170 curves inwardly toward the internal lumen 166 and configuring the annular valve member 176 such that it has a toroid shape. Alternatively, or in addition, a protrusion similar to protrusion 144 may be added to the seal surface 170 around the bypass aperture 174.

It should be noted here that there are a variety of advantages associated with the present inlet and bypass valves 104 and 106. For example, each valve consists of a single machined part (i.e. the inlet valve base 142 portion of the inlet tube 108 and a portion of the pump tube 120) and a single molded part (i.e. the resilient cup-shaped structure 152 and the resilient annular valve member 176). The present two-part designs include fewer parts, and are easier to assemble, as compared to conventional inlet and bypass valves. The configurations of the present inlet and bypass valves 104 and 106 also reduce the ullage associated with the inlet chamber 126, as compared to conventional inlet and bypass valves. Ullage associated with an inlet chamber is problematic because, if air enters the ullage, movement of the piston to the pull-back position (FIGS. 3 and 8) may not result in a sufficient decrease in pressure within the pump chamber to open the inlet valve and/or movement back to the rest position (FIGS. 2 and 11) may not result in a sufficient increase in pressure within the pump chamber to open the bypass valve. In the illustrated embodiment, the ullage associated with the inlet chamber 126 is merely the combined volume of the slots 158 (FIG. 6) and the bypass channel 172 and bypass aperture 174 (FIG. 11). The reduction in ullage increases the expansion ratio during piston pull-back, increase the compression ratio during piston return, and improves bubble handling, as compared to conventional inlet and bypass valves. The ullage of the illustrated embodiment may be minimized by maximizing the depth of the annular indentation 168, thereby minimizing the volume of the bypass aperture 174, to the extent practicable.

The flow channel 130 (FIGS. 2, 10 and 11), which leads from the bypass valve 106 to the outlet chamber 128, may be located between the inner surface 149 of the outer pump tube 116 and the outer surface of the inner pump tube 120. In the illustrated embodiment, the flow channel 130 is defined by a portion to the generally cylindrical main body that, when measured in a direction perpendicular to the longitudinal axis, is smaller than the diameter of the inner surface 149. To that end, the outer surface of the generally cylindrical main body 164 includes a generally planar surface 178 that extends from one longitudinal end of the main body to the other and is aligned with the bypass aperture 174. Flow channels may be formed in other ways. By way of example, but not limitation, a channel may be formed by a groove in the outer surface of the generally cylindrical main body 164. In either case, the flow (or "bypass") channel 130 in the present pump 102 is simply a clearance space between to existing parts of the pump (i.e. the inner and outer pump tubes 120 and 116), which results in smaller, lower profile, and less costly device than conventional pumps that include a separate tube or hole for the bypass channel, such as that shown in aforementioned U.S. Pat. No. 6,796,777 to Falk et al.

In the illustrated embodiment, a second flow channel 130a is defined by a second generally planar surface 178a that extends from one longitudinal end of the main body 164 to the other. The flow channels 130 and 130a are diametrically opposed, i.e. flow channel 130a circumferentially offset from flow channel 130 by 180 degrees. The second flow channel provides a flow path for fluid that may travel around the annular indentation 168 along the outer surface of the resilient annular valve member 176.

The exemplary inner pump tube 120 also include channels 180 (only one shown) on the longitudinal end of the generally cylindrical main body 164 opposite the annular indentation 168. The channels 180 extend from the internal lumen 166 to the planar surfaces 178. The channels 180 provide a path for fluid that may be trapped between the end of the inner pump tube 120 and the piston second cylindrical portion 184 (discussed below with reference to FIGS. 13 and 13A) in order to reduce the amount of force required to move the magnetic piston 122 from the rest position.

Suitable materials for the exemplary inner pump tube 120 are non-magnetic and include, but are not limited to, titanium (e.g. titanium capillary tubing), ceramic and plastics. Ceramics and plastics are also advantageous in that they result in lower eddy current energy losses. The internal lumen 166 may be treated using suitable deposition and/or implantation processes to improve medication compatibility and/or wear resistance. Suitable materials for the resilient annular valve member 176 include, but are not limited to, elastomers with good sealing properties such as low durometer silicone rubber, fluoroelastomers, urethanes, and latex rubber. The elastomers may be coated or treated to reduce adhesion to the seal surface 170.

As illustrated in FIG. 13, the exemplary magnetic piston 122 is a solid, lumen-free structure that includes a first, second and third cylindrical portions 182, 184 and 186. The diameter of the outer surface 187 of the first cylindrical portion 182, which is located within the internal lumen 166 of the inner pump tube 120, is less than the diameter of the outer surface 188 of the second cylindrical portion 184. The diameter of outer surface 188 is less than the diameter of the inner surface 149 of the outer pump tube 116 and a flow channel 190 (FIG. 13A) is defined therebetween. In the illustrated embodiment, the diameter of the outer surface 188 is approximately equal to the distance between the planar surfaces 178 and 178a (FIG. 10). The flow (or "bypass") channel 190 is annularly shaped and is connected to flow channels 130 and 130a. The diameter of the outer surface 192 of the third cylindrical portion 186 is less than the diameter of the outer surface 188.

The clearance between the internal lumen 166 and the first cylindrical portion outer surface 187 is relatively small (about 0.0005 inch in the illustrated embodiment). The small clearance creates a narrow capillary channel that holds liquid and isolates, with respect to the internal lumen 166, the inlet chamber 126 (FIGS. 3 and 8) the outlet chamber 128 (FIGS. 2 and 13A). The liquid also forms a viscous piston ring that, due to the relatively long internal lumen 166/piston 122 interface and the small circumference of the ring, increases backflow resistance. Self-priming of the exemplary pump may be obtained through the selection of the length of the internal lumen 166/piston 122 interface, the stroke length, and the aforementioned clearance.

Suitable materials for the magnetic piston 122 include, but are not limited to, AL29-4 superferritic stainless steel alloy and similar magnetic materials. The materials may, or may not, be pre-magnetized into a permanent magnet. Some or all of the magnetic piston 122 may be treated with a ceramic ion implantation process, the application of diamond-like coating, parylene deposition, or a variety of other processes to obtain improved medication compatibility, greater wear resistance, and improved hydrophilicity.

It should also be noted here that, in other implementations, the magnetic piston 122 may be reconfigured and, where appropriate, the inner pump tube 120 may be modified to accommodate the reconfigured magnetic piston. By way of example, but not limitation, the magnetic piston in an otherwise identical pump may be configured as a solid cylinder that does not vary in diameter and is the same length as the piston 122, and the inner pump tube 120 may be correspondingly lengthened such that it abuts the electromagnet core 134. Also, in the illustrated embodiment, the entire piston 122 (but for any surface coatings) is formed from magnetic material. In other embodiments, one or more portions of the piston may be formed by non-magnetic material. For example, the first cylindrical portion 182 may be formed from a non-magnetic material while the second and third cylindrical portions 184 and 186 are formed from magnetic material. It should also be noted that, in some fluid transfer devices that employ the exemplary inlet valve 104 and/or bypass valve 106, but not pump 102, a non-magnetic piston may be employed.

Referring to FIGS. 13A-15A, in addition to forming part of the electromagnet 118, the core 134 includes a lumen 138 that holds and centers the spring 124 (FIG. 13A), forms part of the fluid flow path, and acts as a piston stop. The exemplary electromagnet core 134 includes a cylindrical main body 194 with a cup-shaped indentation 196 that is enclosed by an annular wall 198 and defines the outlet chamber 128. The lumen 138 extends from the indentation 196 to a spring abutment 200, where the diameter of the lumen decreases. The outer diameter of the cylindrical main body 194 is essentially equal to the diameter of the inner surface 149 of the outer pump tube 116, and the diameter of the outer surface 192 of the third piston portion 186 is less than the inner diameter of the wall 198. As such, fluid from the annular flow channel 190 will flow past the third piston portion 186 and into the outlet chamber 128 when the magnetic piston 122 returns to the rest position (FIG. 13A). Fluid within the outlet chamber 128 is driven into the lumen 138 when the piston moves to the pull-back position (FIG. 3), as is discussed in greater detail below with reference to FIGS. 16-20.

Turning to FIG. 13A, a portion of the magnetic piston 122, the spring 124, and a portion of the electromagnet core 134 form an outlet valve 201 (FIG. 13A) that prevents flow in excessive flow situations (e.g. reservoir overfill or a vacuum applied to the outlet during a diagnostic procedure) and/or where the magnetic piston is being held in the pull-back position for prolonged periods (e.g. the patient and pump are subjected to a strong magnetic field, such as that associated with an MRI). In either case, the outlet valve 201 is closed when the magnetic piston 122 is in the pull-back position against the electromagnet core 134, thereby preventing flow though the lumen 138. More specifically, flow through the pump 102 is prevented when the magnetic piston end surface 204 engages the electromagnet core seal surface 197. In the illustrated implementation, the electromagnet core seal surface 197 has a gasket 202 which improves the seal associated with the outlet valve 201 and quiets the operation of the pump 102. In other implementations, the piston end surface 204 may include a gasket, or the gasket may simply omitted. The gasket 202 may be formed as a discrete element and secured to the associated surface, or may be applied to the associated surface as a coating. Suitable gasket materials include, but are not limited to, elastomers with good sealing properties such as low durometer silicone rubber, fluoroelastomers, urethanes, and latex rubber. Additionally, in some implementations, a small leakage path can be added to the gasket 202 to prevent long term lock-up of the outlet valve 201.

With respect to excessive flow, the exemplary outlet valve 201 prevents flow through the pump 102 when there is a relatively high pressure differential across the pump. The flow rate through the pump 102 corresponds to the pressure differential across the pump and, when the flow rate reaches a predetermined threshold, the associated force on the magnetic piston 122 will overcome the biasing force of the spring 124 and the piston will move to the pull-back position, thereby closing the outlet valve 201 and preventing additional flow. The threshold pressure is a function of the cross-sectional area of the flow channel 190 around the second cylindrical piston portion 184 and the spring constant of the spring 124. Because the deflection of the spring 124 is quite small relative to its length, pressure sufficient to force open the inlet valve 104 and, possibly, the bypass valve 106, will also close the outlet valve 201. Fluid flowing through the narrow gap between the long internal lumen 166 and the piston 122, as well as the narrow flow channel 190 between the piston surface 188 and the inner surface of the outer pump tube 149, produces drag force that acts on the piston and aids in the closing of the outlet valve 201. A pressure differential sufficient to counteract the force of spring 124 will also maintain the outlet valve 201 in the closed state.

Similarly, when an external magnetic field moves the magnetic piston to the pull-back position, the outlet valve 201 will prevent flow through the pump 102. As such, regardless of the reservoir pressure or any other circumstance that results in pressure differential across the pump 102, placement of the pump in a strong magnetic field will not result in uncontrolled flow.

In addition to the above described safety aspects, the outlet valve 201 is also advantageous in that it takes the place of separate safety valves that are often included in infusion devices, either upstream or downstream of the infusion device pump. As such, the outlet valve 201 simplifies and reduces the cost of the associated infusion device by incorporating the safety valve functionality within the pump through the use of structures that are already part of the pump.

The exemplary filter 112 illustrated in FIGS. 2 and 3, which is held between the inlet tubes 108 and 110 by a connector tube 206, prevents particulate contamination from reaching the interface between the inner pump tube 120 and the magnetic piston 122 and interfering with piston movement. Put another way, although the bypass valve 106 and flow channels 130, 130a and 190 allow almost all of the fluid and any particulates therein to avoid the sensitive interface between the inner pump tube 120 and the piston 122, the filter provides additional protection. The filter 112 also prevents bubbles from entering the pump 102.

The exemplary fluid transfer device 100 may be assembled in the following manner. First, various sub-assemblies may be separately assembled, e.g. the resilient cup-shaped structure 152 may be stretched over the inlet valve base 142 on the inlet tube 108, the resilient annular valve member 176 may be stretched and positioned within the annular indentation 168 on the inner pump tube 120, the magnetic piston 122 may be inserted into the inner pump tube, the spring 124 may be inserted into electromagnet core lumen 138, the inlet tube 110 may be welded by weld $W_1$ (or swaged) to the connector tube 206 and the filter 112 positioned therein, and outlet tube 114 may be inserted into the outer pump tube 116 and welded by weld $W_2$ (or swaged) in place (i.e. the location illustrated in FIG. 15A). The end of the outer pump tube 116 opposite the outlet tube 114 is referred to in this paragraph as the "open end." Next, the electromagnet core 134 (with spring 124 and gasket 202) may be inserted into the open end of the outer pump tube 116, followed by the sub-assembly consisting of the inner pump tube 120, magnetic piston 122, and resilient annular valve member 176. The inner pump tube 120 and the core 134 are secured to the outer pump tube 116, thereby fixing the distance between the magnetic piston 122 and the core. This may be accomplished by, for example, press-fitting the inner pump tube 120 and the core 134 into the outer pump tube 116, swaging, spot welding from the outside through the outer pump tube, or adhesive bonding. The sub-assembly consisting of the inlet tube 108 and resilient cup-shaped structure 152 may be inserted into the open end of the outer pump tube 116. The inlet tube 108 may then be secured to the outer pump tube 116 by, for example, a laser weld $W_3$ (or swaging). The sub-assembly consisting of the inlet tube 110, filter 112 and connector tube 206 may then be secured to the inlet tube 108 by weld $W_4$ (or swaging) the connector tube to the inlet tube. The electromagnet 118 may then be positioned over the outer pump tube 116 and secured in place with, for example, adhesive.

There are a variety of advantages associated with a fluid transfer device that may be assembled in this manner. By way of example, by not limitation, only four welds are required to assemble the fluid transfer device 100, while approximately fifteen welds may be required to assembly a conventional fluid transfer device, such as that illustrated in U.S. Pat. No. 6,796,777 to Falk et al., with a pump, an inlet valve and a bypass valve. Additionally, none of the welds associated with the fluid transfer device 100 are located in an area where weld debris could get into flow path and cause the pump to fail, which is not the case in many other fluid transfer devices, including that illustrated in U.S. Pat. No. 6,796,777 to Falk et al.

In an alternative assembly method, which is particularly applicable to those fluid transfer device implementations where the magnetic piston does not vary in diameter and the inner pump tube 120 abuts the electromagnet core 134, the sub-assembly consisting of the inlet tube 108 and resilient cup-shaped structure 152 (with or without the additional sub-assembly consisting of the inlet tube 110, filter 112 and connector tube 206) may be secured to the outer pump tube 116 first. The end of the outer pump tube 116 opposite the inlet tube 108 is referred to in this paragraph as the "open end." The other sub-assemblies may then be inserted into the open end of the outer pump tube 116 in the reverse order of the assembly method described in the preceding paragraph. Next, a spring that will be located between the electromagnet core 134 and the outlet tube 114 (not shown) may be inserted into the open end of the outer pump tube 116. This spring may be a coil spring, a wave spring, a ball-seal spring or a Bellville spring.

Turning to operation, the exemplary fluid transfer device 100 is shown in the rest state in FIGS. 16 and 17. The magnetic piston 122 is in the rest position, the electromagnet 118 is not energized, and the inlet and bypass valves 104 and 106 are both closed. Fluid is located within the flow channels 130, 130a and 190, as well as within the outlet chamber 128. Under normal operating conditions, there will be no flow through the fluid transfer device 100 when the fluid transfer device is in the rest state. Although pressure at the inlet tube 108 in excess of that required to open the inlet valve 104 when the fluid transfer device 100 is in the rest state may be encountered (e.g. as a result of reservoir overpressure in an infusion device), the outlet valve 201 (FIG. 13A), which is formed by a portion of the magnetic piston 122, the spring 124, and a portion of the electromagnet core 134, will close. The opening/closing pressure differential may be made relatively small through the selection of the parameters of spring 124, the diameter of the second cylindrical piston portion 184, the diameter of the outer tube inner lumen 149, and the length of the internal lumen 166 and flow channel 190. This aspect of the exemplary fluid transfer device 100 may also eliminate the need for a separate pressure regulator, which is frequently employed in implantable infusion devices to prevent unintended infusion to the patient.

The exemplary fluid transfer device 100 is actuated by connecting the coil 132 in the electromagnet 118 to an energy source (e.g. one or more capacitors that are being fired). The resulting magnetic field is directed through the core 134 and into, as well as through, the magnetic piston 122. The magnetic piston 122 is attracted to the core 134 by the magnetic field. The intensity of the magnetic field grows as current continues to flow through the coil 132. When the intensity reaches a level sufficient to overcome the biasing force of the spring 124, the magnetic piston 122 will be pulled rapidly toward the core 134, and will compress the spring, until the magnetic piston portion 186 reaches the pull-back position and strikes the gasket 202 (FIGS. 18 and 19). Put another way, in addition to driving fluid from the inlet and outlet chambers 126 and 128, the magnetic piston 122 also performs the function of the armature pole in a conventional electromagnet pump, albeit from a different position relative to the electromagnet, and the electromagnet core 134 also functions as a piston stop.

Movement of the magnetic piston 122 from the rest position illustrated in FIGS. 16 and 17 to the pull-back position illustrated in FIGS. 18 and 19 results in a decrease in pressure in the inlet chamber 126. The coil 132 will continue to be energized for a brief time (e.g. a few milliseconds) in order to hold the magnetic piston 122 in the pull-back position. The reduction in pressure within the inlet chamber 126 will result in a pressure differential across the valve member 160 that will overcome the pretension associated with the stretching of the cup-shaped structure 152 and cause some or all of the valve member to move away from the seal surface protrusion 144, thereby opening the inlet valve 104. Fluid from the inlet tube inner lumen 146 will flow into the inlet chamber 126. The inlet valve 104 will close, due to the pretension of the cup-shaped structure 152, once the pressure within inlet chamber 126 is equal to pressure at the inlet tube inner lumen 146. Because the coil 132 continues to be energized, the magnetic piston will remain in the position illustrated in FIGS. 18 and 19 as fluid flows into the inlet chamber 126 and the inlet valve 104 closes.

Movement of the magnetic piston 122 from the rest position illustrated in FIGS. 16 and 17 to the pull-back position illustrated in FIGS. 18 and 19 also results in fluid exiting the fluid transfer device 100 by way of the outlet tube 114 (FIG. 3) and maintains the bypass valve 106 in a closed state. More specifically, such movement of the magnetic piston 122 increases the pressure in the outlet chamber 128 and drives fluid through the lumen 138 in the electromagnet core 134. The pressure within the flow channels 130, 130a and 190 also increases, which seals the bypass valve 106 more tightly.

Shortly after the inlet valve 104 closes, the coil 132 will be disconnected from the energy source and the magnetic field established by the electromagnet 118 will decay until it can no longer overcome the force exerted on the magnetic piston 122 by the spring 124. The magnetic piston 122 will then move back to the position illustrated in FIGS. 16 and 17, to more firmly hold the inlet valve 104 closed. The associated increase in pressure within the inlet chamber 128 will open the bypass valve 106 by stretching the portion of the resilient annular valve member 176 adjacent to the bypass aperture 174 away from the seal surface 170. Fluid will flow past the annular valve member 176, into the annular indentation 168 and then into the flow channels 130 and 130a. This fluid will ultimately reach the outlet chamber 128 by way of the flow channel 190.

In the exemplary context of implantable drug delivery devices, and although the volume/stroke magnitude may be increased in certain situations, the fluid transfer devices will typically deliver about 1 microliter/stroke or other actuation, but may be more or less (e.g. about 0.25 microliter/actuation or less) depending on the particular fluid transfer device employed.

Although the present fluid transfer devices are not limited to any particular size or application, one example of a fluid transfer device that may be used in an implantable infusion device ("the exemplary configuration") may be sized as follows. Referring to FIGS. 4-7, the inlet tube 108 in the exemplary configuration has a main portion 140 that is about 0.25 inch in length and about 0.093 inch in diameter, an inlet valve base 142 that is about 0.059 inch in length and about 0.086 inch in diameter, a protrusion 144 that extends about 0.001 inch from the seal surface 143, and an inner lumen 146 that is about 0.010 inch in diameter. The resilient cup-shaped structure 152 in the exemplary configuration is about 0.063 inch in length has an unstressed diameter that is about 0.075 inch (i.e. about 50%-95% of the valve base diameter) and is about 0.003 inch thick. The diameter of the movable valve member 160 is about 0.016 inch. Turning to FIGS. 9 and 10, the inner pump tube 120 in the exemplary configuration is about 0.260 inch in length and about 0.093 inch in diameter, and has a main body 164 that is about 0.236 inch in length, an internal lumen 166 that is about 0.050 inch in diameter, an annular indentation 168 that is about 0.014 inch in length and about 0.083 inch in diameter, a bypass aperture 174 that is about 0.005 inch in diameter, and planar surfaces 178 that are about 0.026 inch wide (measured perpendicular to the longitudinal axis of the inner pump tube) which creates a maximum distance between the planar surfaces 178 and the outer pump tube inner surface 149 of about 0.003 inch. Referring to FIGS. 13-15, the magnetic piston 122 in the exemplary configuration has a first cylindrical portion 182 that is about 0.254 inch in length and about 0.050 inch in diameter, a second cylindrical portion 184 that is about 0.127 inch in length and about 0.087 inch in diameter, and a third cylindrical portion 186 that is about 0.013 inch in length and about 0.077 inch in diameter.

The flow channel 190 is about 0.003 inch thick. The electromagnet core 134 in the exemplary configuration is about 0.196 inch in length and about 0.093 inch in diameter, and has a cup-shaped indentation 196 that is about 0.013 inch deep and about 0.083 inch in diameter and a lumen 138 that is about 0.026 inch in diameter and about 0.170 inch in length. The surface 197 is separated from the piston end surface 204 by about 0.013 inch when the pump 102 is in the rest state. The spring 124 has a free length of about 0.196 inch and a spring constant of about 1 g/0.001 inch. As such, the spring 124 is compressed about 0.013 inch when the pump is at rest, which creates a 13 g preload. Given that the inner lumen 146 (which serves as the inlet) is about 0.010 inch in diameter, the forced opening pressure is about 369 psi and, accordingly, the present fluid transfer device is more tolerant of reservoir overpressure than conventional fluid transfer devices with larger inlet diameters. It should be noted here that the relatively small inlet diameter is facilitated by the fact that portions of the inlet valve are not located within the inlet, as is the case in many conventional fluid transfer devices. Turning to FIGS. 3 and 3A, the axial length $AL_{case}$ of the electromagnet case 136 in the exemplary configuration is about 0.380 inch, and the outer pump tube 116 is about 0.900 inch in length and has an inner diameter of about 0.093 inch.

Another exemplary fluid transfer device in accordance with at least one of the present inventions is generally represented by reference numeral 100a in FIGS. 21 and 22. The exemplary fluid transfer device 100a is similar in many respects to the fluid transfer device 100 and similar elements are represented by similar reference numerals. The description above of such similar elements is incorporated by reference into this portion of the present specification. To that end, the fluid transfer device 100a includes a pump 102a, an inlet tube 110 associated with one end of the pump, and an outlet tube 114 associated with the other end. The exemplary pump 102a has an outer pump tube 116, an electromagnet 118a that has a portion carried within the outer pump tube and a portion carried on the exterior of the outer pump tube, and a magnetic piston 122a. The magnetic piston 122a is biased to the rest position illustrated in FIG. 21 by a spring 124. The pump 102a also has an inlet chamber 126 (FIG. 22) and an outlet chamber 128 (FIG. 21). Movement of the magnetic piston 122a to the pull-back position illustrated in FIG. 22 results in a decrease in pressure in the inlet chamber 126, which causes fluid to flow into the inlet chamber. Movement of the magnetic piston 122a to the pull-back position also drives fluid out of the outlet chamber 128 and through the electromagnet core 134a (discussed below). When the magnetic piston 122a moves back to the rest position, the pressure within the inlet chamber 126 will increase and fluid will flow through the capillary interface 208 between the pump tube 116 and the piston 122a to the outlet chamber 128.

The exemplary electromagnet 118a includes a coil 132, a core 134a and a case 136. In addition to forming part of the electromagnet 118a, the core 134a includes a lumen 138 that centers the spring 124, forms part of the fluid flow path, acts as a piston stop, and forms part of a one-way outlet valve 210. To that end, and referring to FIGS. 21-24, the electromagnet core 134a has a main portion 212 and a valve base 214 with a seal surface 216 that has a protrusion 218. The outer diameter of the main portion 212 is essentially equal to the inner diameter of the outer pump tube 116. A pre-tensioned resilient cup-shaped structure 152, with a cylindrical wall 154, an end wall 156, various slots and a movable valve member 160, is configured and carried on the valve base 214 in the manner described above with respect to the inlet valve 104. The pretension pulls the end wall 156, including the movable valve member 160, against the seal surface 216 and seal surface protrusion 218, thereby closing the one-way valve 210 and preventing backflow from the outlet tube 114 to the pump 102a (FIG. 23). In those instances where a negative pressure reservoir is employed, the negative pressure will also pull the movable valve member 160 to the closed position. The one-way valve 210 is opened (FIG. 24) when movement of the magnetic piston 122a to the pull-back position drives fluid into, and increases the pressure within, the electromagnet core lumen 138. The valve 210 will re-close when the pressure within the electromagnet core lumen 138 drops.

It should also be noted that a filter (e.g. filter 112) may be mounted on the inlet end of the inlet tube 110 in a manner similar to that described above with reference to FIGS. 2 and 3. Also, in other implementations, a valve such as a poppet valve, a duckbill valve, or a check valve, may be employed in place of the exemplary one-way outlet valve 210.

It should be noted here that although the various elements of the exemplary fluid transfer devices are annular or circular in cross-sectional shape, the present inventions are not so limited.

One example of an infusion device that may employ the exemplary fluid transfer device 100 (or 100a) is the implantable infusion device generally represented by reference numeral 300 in FIGS. 25-28. As used herein, an "infusion device" is a device that includes a permanent or replaceable reservoir, a fluid transfer device and an outlet, and an "implantable infusion device" is an "infusion device" with a permanent reservoir that is sized, shaped and otherwise constructed (e.g. sealed) such that both the reservoir and outlet can be simultaneously carried within the patient's body. The exemplary infusion device 300 includes a housing 302 (e.g. a titanium housing) with a bottom portion 304, an internal wall 306, and a cover 308. An infusible substance (e.g. medication) may be stored in a reservoir 310 that is located within the housing bottom portion 304. The reservoir 310 may be replenished by way of a fill port 312 that extends from the reservoir to the cover 308. A hypodermic needle (not shown), which is configured to be pushed through the fill port 312, may be used to replenish the reservoir 310. Fluid flow from the fill port 312 to the reservoir 310 may be controlled by an inlet valve (not shown).

A wide variety of reservoirs may be employed. In the illustrated embodiment, the reservoir 310 is in the form of a titanium bellows that is positioned within a sealed volume defined by the housing bottom portion 304 and internal wall 306. The remainder of the sealed volume is occupied by propellant P, which may be used to exert negative pressure on the reservoir 310. Other reservoirs that may be employed in the present infusion devices include reservoirs in which propellant exerts a positive pressure. Still other exemplary reservoirs include negative pressure reservoirs that employ a movable wall that is exposed to ambient pressure and is configured to exert a force that produces an interior pressure that is always negative with respect to the ambient pressure.

The exemplary ambulatory infusion device 300 illustrated in FIGS. 25-28 also includes the fluid transfer device 100. The inlet of the fluid transfer device 100 is coupled to the interior of the reservoir 310 by a passageway 317, while the outlet of the fluid transfer device is coupled to an outlet port 318 by a passageway 320. Operation of the fluid transfer device 100 causes infusible substance to move from the reservoir 310 to the outlet port 318. A catheter 324 may be connected to the outlet port 318 so that the infusible substance passing through the outlet port will be delivered to a target body region in spaced relation to the infusion device 300 by way of the outlet 325 at the end of the catheter.

Energy for the fluid transfer device 100, as well for other aspects of the exemplary infusion device 300, is provided by the battery 326 illustrated in FIG. 26. In the specific case of the fluid transfer device 100, the battery 326 is used to charge one or more capacitors 328, and is not directly connected to the fluid transfer device itself. The capacitor(s) 328 are connected to the electromagnet coil 132 in the fluid transfer device 100, and disconnected from the battery 326, when the electromagnet coil is being energized, and are disconnected from the electromagnet coil and connected to the battery when the capacitor(s) are being recharged and/or when the fluid transfer device is at rest. The capacitor(s) 328 are carried on a board 330. A communication device 332, which is connected to an antenna 334, is carried on the same side of the board 330 as the capacitor(s) 328. The exemplary communication device 332 is an RF communication device. Other suitable communication devices include, but are not limited to, oscillating magnetic field communication devices, static magnetic field communication devices, optical communication devices, ultrasound communication devices and direct electrical communication devices.

A controller 336 (FIG. 28), such as a microprocessor, microcontroller or other control circuitry, is carried on the other side of the board 330. The controller controls the operations of the infusion device 300 in accordance with instructions stored in memory 338 and/or provided by an external device by way of the communication device 332. For example, the controller 336 may be used to control the fluid transfer device 100 to supply fluid to the patient in accordance with, for example, a stored delivery profile or a bolus delivery request (generically referred to as a "delivery instruction"). The controller 336 may also be used to monitor and/or calculate pressure, to calculate the volume of fluid supplied with each actuation of the fluid transfer device 100, and to perform other analytical functions.

Referring to FIGS. 25, 26 and 28, the exemplary infusion device 300 is also provided with a side port 340 that is connected to the passageway 320 between the outlet of the fluid transfer device 100 and the outlet port 318. The side port 340 facilitates access to an implanted catheter 324, typically by way of a hypodermic needle. For example, the side port 340 allows clinicians to push fluid into the catheter 324 and/or draw fluid from the catheter for purposes such as checking catheter patency, sampling CSF, injecting contrast dye into the patient and/or catheter, removing medication from the catheter prior to dye injection, injecting additional medication into the region at the catheter outlet 325, and/or removing pharmaceuticals or other fluids that are causing an allergic or otherwise undesirable biologic reaction.

The outlet port 318, a portion of the passageway 320, the antenna 334 and the side port 340 are carried by a header assembly 342. The header assembly 342 is a molded, plastic structure that is secured to the housing 302. The housing 302 includes a small aperture through which portions of the passageway 320 are connected to one another, and a small aperture through which the antenna 334 is connected to the board 330.

The exemplary infusion device 300 illustrated in FIGS. 25-28 also includes a pressure sensor 344 that is connected to the passageway 320 between the outlet of the fluid transfer device 100 and the outlet port 318. As such, the pressure sensor 344 senses the pressure at the outlet port 318 which, in the illustrated embodiment, is also the pressure within the catheter 324. The pressure sensor 344 is connected to the controller 336 and may be used to analyze a variety of aspects of the operation of the exemplary implantable infusion device 300. An audible alarm 346, which is located within the housing 302, is also connected to the controller 336.

Although the inventions disclosed herein have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

I claim:

1. An infusion device, comprising:
a fluid transfer device including
an electromagnet including a coil having an inner-most diameter that defines an internal volume, a case defining an internal volume in which the coil is located, and a core having a fluid lumen, with an inlet and an outlet, extending therethrough, at least a portion of the core located within the internal volume defined by the case, and
a piston that is movable relative to the core between a rest position and a pull-back position adjacent to the core and is biased to the rest position, the piston having a magnetic portion that is located within the volume defined by the inner-most diameter of the coil;
an infusion device outlet operably connected to the fluid transfer device; and
a reservoir operably connected to the fluid transfer device such that the fluid transfer device receives fluid from the reservoir.

2. An infusion device as claimed in claim 1, further comprising:
an infusion device housing; and
wherein the fluid transfer device and the reservoir are located within the infusion device housing.

3. An infusion device as claimed in claim 1, wherein the reservoir comprises a negative pressure reservoir.

4. An infusion device as claimed in claim 1, wherein the piston includes first and second longitudinal ends and does not include a fluid lumen extending therethrough.

5. An infusion device as claimed in claim 4, further comprising:
an inlet chamber associated with the first longitudinal end of the piston;
an inlet valve associated with the inlet chamber;
a bypass valve associated with the inlet chamber; and
a bypass channel extending from the bypass valve to the second longitudinal end of the piston.

6. An infusion device as claimed in claim 1, wherein the entire piston is magnetic and less than all of the piston is located within the volume defined by the inner-most diameter of the coil.

7. An infusion device as claimed in claim 1, further comprising:
a spring that biases the piston to the rest position.

8. An infusion device as claimed in claim 7, wherein at least a portion of the spring is located with the electromagnet core fluid lumen.

9. An infusion device as claimed in claim 1, wherein
the core includes a seal surface that extends around the fluid lumen inlet;
the piston defines first and second longitudinal ends, the second longitudinal end of the piston facing the core seal surface; and
the fluid transfer device further comprises a gasket carried by the core seal surface or the second longitudinal end of the piston such that the gasket is in contact with the core seal surface and the second longitudinal end of the piston when the piston is in the pull-back position.

10. An infusion device, comprising:
a fluid transfer device including
an electromagnet including a coil, a case defining an internal volume, and a core formed from magnetic material and having a fluid lumen, with an inlet and an outlet, extending therethrough, at least a portion of the core located within the internal volume defined by the case,
a piston having a portion that is magnetic and is located within the internal volume defined by the case, movable relative to the core between a rest position and a pull-back position adjacent to the core, and biased to the rest position, and
an outer pump tube,
wherein the coil is carried outside the outer pump tube and the core and the piston are carried inside the outer pump tube;
an infusion device outlet operably connected to the fluid transfer device; and
a reservoir operably connected to the fluid transfer device such that the fluid transfer device receives fluid from the reservoir.

11. An infusion device as claimed in claim 10, further comprising:
an inner pump tube located within the outer pump tube and defining a piston lumen, at least a portion of the piston being located within the piston lumen.

12. An infusion device as claimed in claim 11, wherein
the piston defines first and second longitudinal ends;
an inlet chamber is defined by the piston lumen and the first longitudinal end of the piston;
an outlet chamber is defined by the second longitudinal end of the piston and the electromagnet core;
a bypass channel, at least a portion of which is defined by the inner and outer pump tubes, connects the inlet chamber to the outlet chamber; and
a bypass valve is associated with the inlet chamber and the bypass channel.

13. An infusion device as claimed in claim 12, wherein the electromagnet core, the piston, the inner pump tube and the outer pump tube define a common longitudinal axis.

14. An infusion device, comprising:
a fluid transfer device including
an outer pump tube defining an inner surface,
an inner pump tube located within the outer pump tube and defining a piston lumen and an outer surface,
a piston which defines first and second longitudinal ends and a longitudinally extending outer surface, does not include a fluid lumen extending therethrough, and has at least a portion thereof mounted within the piston lumen such that the piston lumen and the first longitudinal end define an inlet chamber and a longitudinally extending capillary seal is formed between the longitudinally extending outer surface of the piston and the inner pump tube,
an electromagnet including a coil carried outside the outer pump tube and a core formed from magnetic material and having a fluid lumen, with an inlet and an outlet, carried inside the outer pump tube such that an outlet chamber is defined between the second longitudinal end of the piston and the core,
a bypass channel, defined at least in part by in the outer surface of the inner pump tube and the inner surface of the outer pump tube, that connects the inlet chamber and the outlet chamber, and
a bypass valve associated with the inner pump tube, the inlet chamber and the bypass channel;
an infusion device outlet operably connected to the fluid transfer device; and
a reservoir operably connected to the fluid transfer device such that the fluid transfer device receives fluid from the reservoir.

15. An infusion device as claimed in claim 14, further comprising:

an infusion device housing; and
wherein the fluid transfer device and the reservoir are located within the infusion device housing.

16. An infusion device as claimed in claim 14, wherein the reservoir comprises a negative pressure reservoir.

17. An infusion device as claimed in claim 14, further comprising:
an inlet valve associated with the inlet chamber.

18. An infusion device as claimed in claim 17, further comprising:
an inlet tube, including a portion of the inlet valve, secured to the outer pump tube.

19. An infusion device as claimed in claim 18, wherein
the inlet valve includes an inlet valve base, defining a lumen and a seal surface, that is part of the inlet tube; and
the inlet valve includes a resilient structure, mounted in tension on the valve base, including a valve member movable between a closed state where the valve member engages the seal surface and an open state where at least a portion of the valve member is spaced apart from the seal surface.

20. An infusion device as claimed in claim 19, wherein the piston is movable between a rest position where the first longitudinal end is in contact with the inlet valve resilient structure and a pull-back position where the second longitudinal end is in contact with the core.

21. An infusion device as claimed in claim 14, wherein at least a portion of the piston is formed from magnetic material.

22. An infusion device as claimed in claim 21, further comprising:
a spring, located within the magnetic core lumen, that biases the piston to the rest position.

23. An infusion device as claimed in claim 14, wherein
the inner pump tube defines an outer surface, a perimeter and a bypass aperture with an inlet associated with the inlet chamber and an outlet associated with the inner pump tube outer surface; and
the bypass valve includes a resilient valve member that extends around the perimeter of the inner tube outer surface and over the bypass aperture outlet.

24. An infusion device as claimed in claim 14, wherein
the inner pump tube defines an outer surface with a longitudinally extending substantially planar portion;
the outer pump tube defines an inner surface; and
the bypass channel is defined at least in part by the outer pump tube inner surface and the substantially planar portion of inner pump tube outer surface.

25. An infusion device as claimed in claim 24, wherein
a portion of the piston is located outside the piston lumen and defines an outer surface; and
the bypass channel is defined in part by the outer pump tube inner surface and the outer surface of the portion of the piston located outside the piston lumen.

26. An infusion device as claimed in claim 14, wherein the electromagnet core defines a cup-shaped indentation configured to receive the second longitudinal end of the piston.

27. An infusion device as claimed in claim 14, wherein the electromagnet core, the piston, the inner pump tube and the outer pump tube define a common longitudinal axis.

28. An infusion device, comprising:
a fluid transfer device including
a housing defining a piston lumen,
a piston stop formed at least in part from magnetic material, located within the housing, and including a fluid lumen defining an inlet and an outlet,
an inlet valve located within the housing,
an electromagnet coil carried on the housing,
a piston which defines first and second longitudinal ends, does not include a fluid lumen extending therethrough, is formed at least in part from magnetic material, and has at least a portion thereof mounted within piston lumen such that the first longitudinal end and the piston lumen together define an inlet chamber having a volume and the second longitudinal end and the piston stop together define an outlet chamber,
the piston being movable between a first position, where the volume of the inlet chamber is minimized and the first longitudinal end abuts the inlet valve, and a second position, where the second longitudinal end of the piston abuts the piston stop and the prevents flow into the inlet of the piston stop lumen, and
a spring that biases the piston to the first position, at least a portion of the spring being located within the piston stop fluid lumen;
an infusion device outlet operably connected to the fluid transfer device; and
a reservoir operably connected to the fluid transfer device such that the fluid transfer device receives fluid from the reservoir.

29. An infusion device as claimed in claim 28, further comprising:
an infusion device housing; and
wherein the fluid transfer device and the reservoir are located within the infusion device housing.

30. An infusion device as claimed in claim 28, wherein the reservoir comprises a negative pressure reservoir.

31. An infusion device as claimed in claim 28, wherein the housing includes an outer pump tube and an inner pump tube, located within the outer pump tube, that defines the piston lumen.

32. An infusion device as claimed in claim 28, further comprising:
a bypass valve associated with the inlet chamber; and
a bypass channel extending from the bypass valve to the outlet chamber.

33. An infusion device as claimed in claim 28, wherein piston stop defines a cup-shaped indentation configured to receive the second longitudinal end of the piston.

34. An infusion device as claimed in claim 28, wherein
the piston is biased to the first position by a bias force; and
the piston and piston lumen are configured such that the piston will move to the second position in response to an application of a predetermined pressure across the fluid transfer device.

35. An infusion device as claimed in claim 1, wherein
the piston defines a maximum outer diameter; and
the maximum outer diameter of the piston is less than the inner-most diameter of the coil.

36. An infusion device as claimed in claim 1, wherein
the coil defines a longitudinal axis and longitudinal ends; and
the electromagnet includes a magnetic gap with a portion thereof located mid-way between the longitudinal ends of the coil.

37. An infusion device as claimed in claim 14, wherein
the entire bypass valve is located inwardly of the inner surface of the outer tube.

* * * * *